United States Patent [19]

Lalonde et al.

[11] Patent Number: 5,536,858
[45] Date of Patent: Jul. 16, 1996

[54] TETRASULFONATED DIPHOSPHINE COMPOUNDS AND METAL COMPLEXES THEREOF FOR ASYMMETRIC CATALYTIC REACTIONS

[75] Inventors: Michel Lalonde, Basel; Rudolf Schmid, Arlesheim, both of Switzerland

[73] Assignee: Hoffmann-La Roche Inc., Nutley, N.J.

[21] Appl. No.: 349,107

[22] Filed: Dec. 2, 1994

[30] Foreign Application Priority Data

Feb. 12, 1994 [EP] European Pat. Off. ............... 94102192

[51] Int. Cl.$^6$ ........................... C07F 9/28; C07F 15/00
[52] U.S. Cl. ............................................... 556/21; 562/35
[58] Field of Search .............................. 562/35; 556/21

[56] References Cited

U.S. PATENT DOCUMENTS

| | | | |
|---|---|---|---|
| 5,274,146 | 12/1993 | Ishizaki et al. | 556/14 |
| 5,274,183 | 12/1993 | Herrman et al. | 562/35 |
| 5,324,861 | 6/1994 | Ishizaki et al. | 568/454 |
| 5,347,045 | 9/1994 | Hermann et al. | 562/35 |

FOREIGN PATENT DOCUMENTS 0544455  6/1993  European Pat. Off. .

OTHER PUBLICATIONS

Wan, et al, Asymmetric Hydrogenation in Water by a Rhodium Complex of Sulfonated 2,2'-Bis(diphenylphosphine)-1,1'-binaphthyl (binap), J. Chem. Soc. Commun, pp. 1262–1264 (1993).
Kalck, et al, Use of Water–Soluble Ligands in Homogeneous Catalysis, Advances In Organometallic Chemistry, vol. 34 pp. 219–285, (1992).
Schmid, et al, Asymmetric Hydrogenation In Process Research And Development Of Pharmaceuticals, Vitamins And Fine Chemicals, Presentation held at International Symposium on Organic Synthesis (9th Nozaki Conference), Kyoto, JP, Jun. 3–4, 1994.
Ostsuka Symposium "New Aspect Of Organic Chemistry", Tokushima, JP, Jun. 6–7, 1994; this presentation will also be held at the Chiral Europe '94–Symposium, Nice France, Sep. 19–20, 1994.
Broger, et al, "Synthesis Of A Water–Soluble Atropisomeric Diphosphine Ligand And Its Evaluation In Asymmetric Hydrogenation" poster presentation at NATO Advanced Research Workshop On Aqueous Organometallic Chemistry And Catalysis, Debrecen, Hungary, Aug. 29 to Sep. 1, 1994.

*Primary Examiner*—Nicky Chan
*Attorney, Agent, or Firm*—George M. Gould; William H. Epstein; Bruce A. Pokras

[57] ABSTRACT

The invention is concerned with novel water-soluble racemic or optically active compounds of formulae

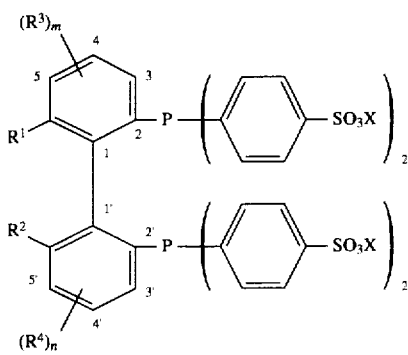

and

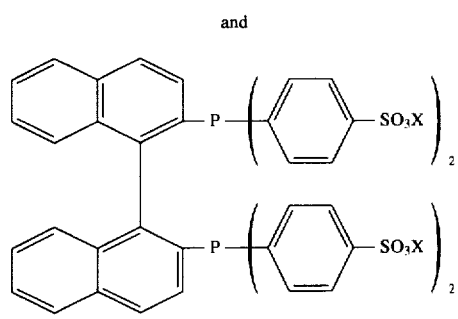

wherein
$R^1$, $R^2$, $R^3$ and $R^4$ independently signify lower alkyl or lower alkoxy;
m and n are 0, 1 or 2; and
X signifies hydrogen, an alkali metal, the equivalent of an earth alkali metal or an ammonium ion;
with the provision that $R^3$ is in position 4 or 5 and $R^4$ is in position 4' or 5'. The invention is also concerned with complexes of such compounds with a metal of Group VIII. These complexes are useful as catalysts for asymmetric hydrogenation and for enantioselective hydrogen displacement in prochiral allylic systems.

19 Claims, No Drawings

TETRASULFONATED DIPHOSPHINE COMPOUNDS AND METAL COMPLEXES THEREOF FOR ASYMMETRIC CATALYTIC REACTIONS

BACKGROUND OF THE INVENTION

The present invention is concerned with novel water-soluble racemic or optically active tetrasulfonated diphosphine compounds of the formulae

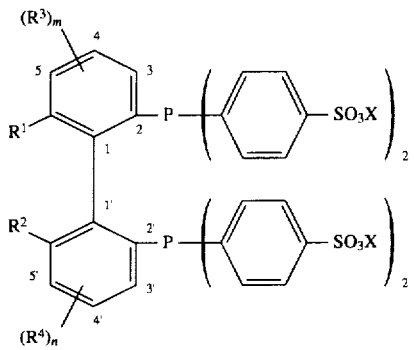

I and

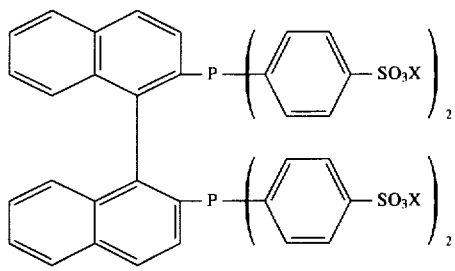

II wherein
$R^1$, $R^2$, $R^3$ and $R^4$ independently signify lower alkyl or lower alkoxy;
m and n are 0, 1 or 2; and
X signifies hydrogen, an alkali metal, an earth alkali metal or an ammonium ion;
with the provision that $R^3$ is located in position 4 or 5, and $R^4$ is located in position 4' or 5'.

The invention is also concerned with the manufacture of compounds of formulae I and II, particularly in their optically active form, i.e. in the (R)- and the (S)-form. Furthermore the invention is concerned with complexes of compounds of formulae I and II, particularly in their optically active forms ((R)- and (S)-form) with transition metals of Group VIII, especially with ruthenium, rhodium, palladium or iridium. These complexes are useful as homogeneous catalysts in asymmetric reactions such as e.g. asymmetric hydrogenation, enantioselective isomerisation, and the like.

It is known that separation of the catalyst from the reaction products and recovery of the catalyst are, next to the activity and selectivity of the catalyst, of major importance to industrial applications of homogeneous catalytic processes. Although catalyst separation is sometimes readily achieved, e.g. in the case of volatile products which can be distilled from the catalyst, it may be more difficult in the case of crystalline products, where co-crystallisation or inclusion may cause problems resulting in intolerable amounts of metal traces in the reaction product. Catalyst recovery and catalyst recycling are generally difficult to achieve in an economically and ecologically-sound way, but are of paramount importance in catalytic reactions which require relatively large amounts of catalyst.

To resolve the problem of catalyst recovery and catalyst recycling, two major approaches—each of its own attractiveness—exist. One of them is the heterogenization of a homogeneous catalyst by anchoring the catalyst or catalyst precursor to an inert support. However, decreasing activity of the heterogenized catalyst due to metal leaching into solution is often observed. A second approach has lead to the development of complexes of water-soluble ligands with transition-metals as catalysts. Such complexes can be used in various ways, e.g. in aqueous solvent systems, in biphasic systems consisting of water and a non-miscible organic phase or in organic systems alone with a subsequent removal of the catalyst by aqueous extraction. Biphasic systems with or without cosolvents, with recycling of the aqueous phase containing the catalyst, recently have been introduced into technical practice. For example, a water-soluble rhodium-phosphine complex, e.g., the sodium salt tris(m-sulfonatophenyl)phosphine), has been used as a catalyst in the preparation of aldehydes by hydroformylation of olefins. The use of such catalysts comprised of water-soluble ligands complexed to transition metals does not only resolve the catalyst-product separation but does contribute to the economy and ecology of the processes by using water as a benign solvent. However, these water-soluble transition metal-phosphine catalysts in the prior art have limited use as catalysts for asymetric reactions, since the sulfonato groups located in the meta position cause steric effects on the asymmetric induction in these reactions.

SUMMARY OF THE INVENTION

This invention is directed to novel tetrasulfonated diphosphine derivatives complexed to transition-metals where the sulfonate groups are located in the para position. The present invention is concerned with novel water-soluble racemic or optically active tetrasulfonated diphosphine compounds of the formulae

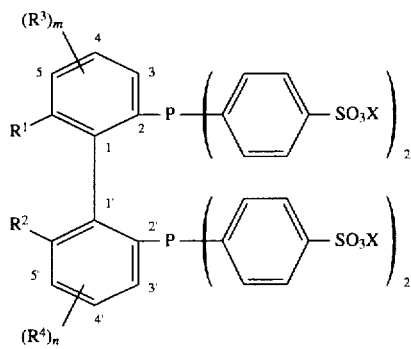

I and

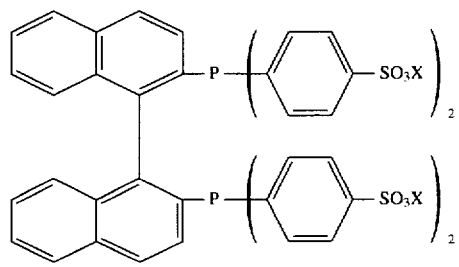

II wherein $R^1$, $R^2$, $R^3$ and $R^4$ independently signify lower alkyl or lower alkoxy;

m and n are 0, 1 or 2; and

X signifies hydrogen, an alkali metal, an earth alkali metal or an ammonium ion;

with the proviso that $R^3$ is located in position 4 or 5, and $R^4$ is located in position 4' or 5'.

The invention is also concerned with the manufacture of compounds of formulae I and II, particularly in their optically active form, i.e. in the (R)- and the (S)-form. Furthermore the invention is concerned with complexes of compounds of formulae I and II, particularly in their optically active forms ((R)- and (S)-form) with transition metals of Group VIII, especially with ruthenium, rhodium, palladium or iridium. These complexes are useful as homogeneous catalysts in asymmetric reactions such as e.g. asymmetric hydrogenation, enantioselective isomerisation, and the like.

DETAILED DESCRIPTION OF INVENTION

The water-solubility of the presently claimed compounds of formulae I and II is achieved by the four sulfonato groups located in the para position of the phenyl groups attached to the phosphorus atoms. It has been found that the para position minimizes or even excludes steric effects of the sulfonato substituents on the spatial arrangement of the phenyl groups in the ligand-derived metal complexes. In addition it has been found that the so-formed tetrasulfonated ligands of formulae I and II have co-ordination properties toward transition-metals similar to the corresponding neutral, non-sulfonated diphosphine derivatives. Thus, complexes derived from the tetrasulfonated ligands of formulae I and II show high activities and high enantioselectivities in asymmetric reactions. This is in contrast to the known chiral water-soluble diphosphine ligands which contain sulfonato-substituents in the meta position of the phenyl groups attached to the phosphorus atoms.

The term "lower alkyl" signifies in accordance with the present invention straight chain alkyl groups with 1 to 4 carbon atoms, i.e. methyl, ethyl, propyl or butyl.

The term "lower alkoxy" refers to any straight chain alkoxy group having 1 to 4 carbon atoms. Preferred lower alkoxy groups are methoxy or ethoxy.

In accordance with this invention, X can be any alkali metal or any earth alkali metal. The preferred earth alkali metal is sodium.

Further are preferred compounds of formulae I, wherein m and n are 0 and wherein $R^1$ and $R^2$ are the same and signify methyl or methoxy. Especially preferred are compounds of formula I, wherein m and n are 0 and $R^1$ and $R^2$ are methoxy.

According to the invention, compounds of formula I are prepared as depicted in Scheme I below:

Scheme 1

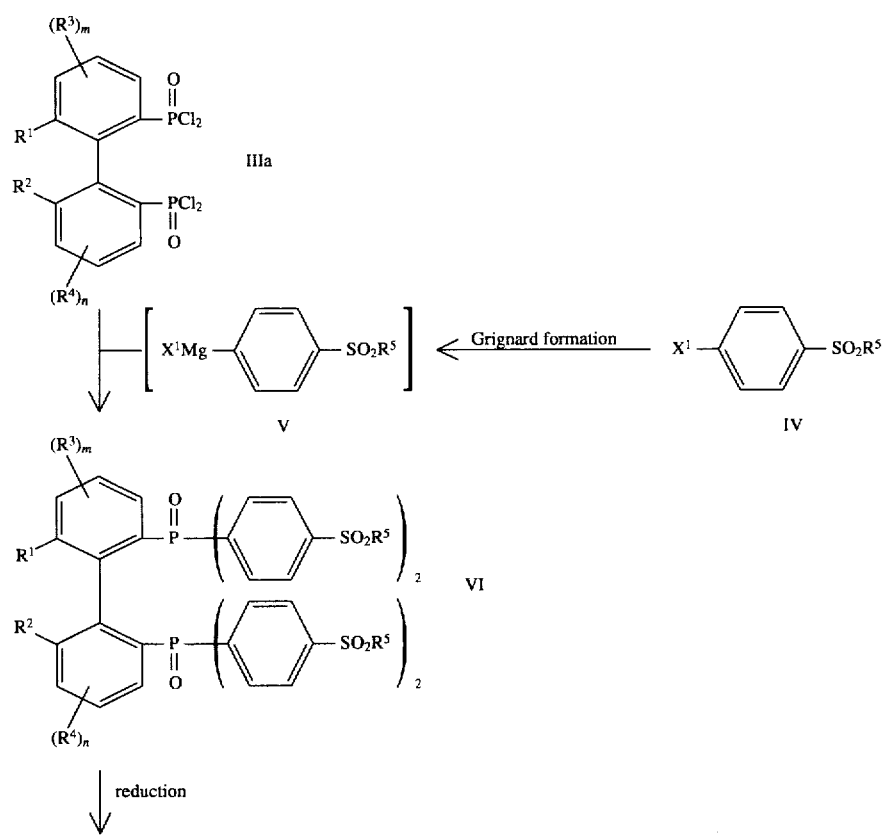

-continued
Scheme 1

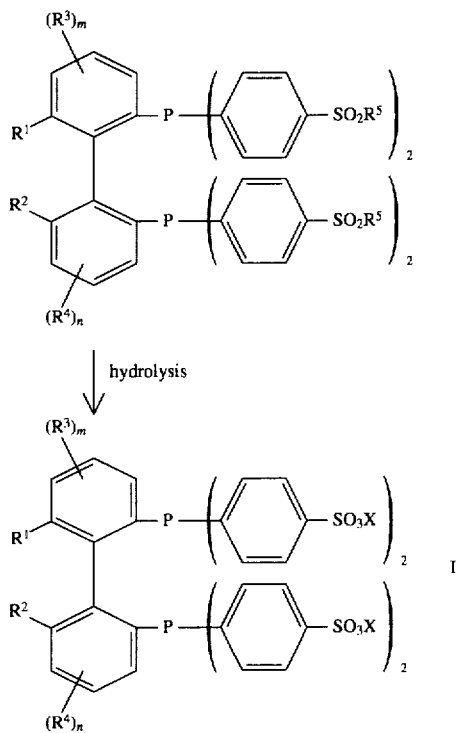

In accordance with this scheme depicted above, $R^1$, $R^2$, $R^3$, $R^4$, X, m and n are as given above. $X^1$ is any halogen, such as bromine or iodine. $R^5$ represents a protecting group for the sulfonato group. As used in this reaction any protecting group may be used, so long as the protecting group is stable both to the Grignard reaction and the reduction conditions applied in the preparation of the compounds of formula I according to the Scheme I. Examples of suitable protecting groups for the sulfonate group are 1-indolyl, 1-pyrrolyl and the like.

In a first step a racemic or optically active derivative of (biphenyl-2,2'-diyl)bis(phosphonic dichloride) (IIIa) is reacted under Grignard conditions known in the art with at least 4 equivalents of a phenyl-Grignard reagent (V) containing a protected sulfonato group in the para position to produce bis(phosphine oxide) of formulae (VI). A particularly favorable and mild preparation method for the phenyl-Grignard reagent (V) is the reaction of a compound of formula IV in e.g. tetrahydrofuran with a slight excess of butyllithium in an apolar solvent like hexane, followed by the addition of $MgBr_2 \cdot EtO_2$ at $-78°$ C.

Subsequently the resulting bis(phosphine oxide) (VI) is reduced to the corresponding bis(phosphine) of formula (VII) by methods known in that art. This reduction can be effected, for example, by reacting the bis(phosphine oxide)(VI) with a silane in an organic solvent in the presence of an auxilliary base. Any silane may be used to reduce the bis(phosptine oxide)(VI). Best results are obtained using trichlorosilane. As used for the reduction, any organic solvent may be used. The preferred organic solvents are aromatic hydrocarbons. Best results are obtained using boiling xylene or alternatively acetonitrile. Any auxilliary base may be used. The preferred auxilliary bases are tributylamine or triethylamine. If desired, this reduction can also be carried out in an autoclave under pressure. Next, the protesting group of the resulting bis(phosphines) of formula VII can be removed in a last step by cleaving the protecting group by hydrolysis in a manner known per se.

The preparation of the starting compound of formula IIIa is described in EP-A-530 335.

According to the invention, compounds of formula II can be prepared in an analogous manner as described above to produce the compounds of formula I in accordance with Scheme I starting from a compound of formula

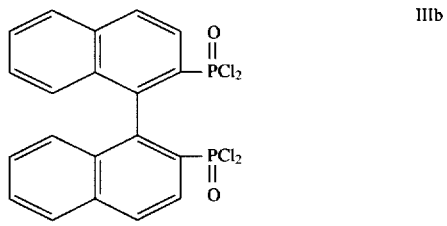

IIIb

The compounds of formulae I and II in accordance with the invention form complexes with transition metals of Group VIII, especially with ruthenium, rhodium, palladium or iridium to form transition metal tetrasulfonated disphosphine complexes. These complexes can be used as catalysts in asymmetric catalytic reactions, especially in asymetric hydrogenations of prochiral compounds with a carbon-carbon, a carbon-oxygen or a carbon-nitrogen double bond, for example compounds which contain one of the groups >C=C<, >C=O, >C=N—, >C=C—N<. Any transition metal of Group VIII may be Used. The preferred complexes for asymmetric hydrogenation of prochiral compounds are complexes containing ruthenium, rhodium or iridum as the transition metals. These catalysts, i.e. complexes from a metal of Group VIII and the compounds of formulae I and II, are novel and also an object of the present invention.

The aforementioned transition metal tetrasulfonated diphosphine complexes can be manufactured in a manner known per se, e.g. by reacting a compound of formulae I or II with any compound which can yield a metal of Group VIII, in a suitable, inert organic or aqueous solvent. Any inert organic or aqueous solvent may be used. As suitable compounds which yield a metal of Group VIII, e.g. rhodium, there can be mentioned, for example, organic rhodium complexes with ethylene, propylene and the like, as well as with bis-olefins, e.g. (Z,Z)-1,5-cyclooctadiene, 1,5-hexadiene, bicyclo[2.2.1]hepta-2,5-diene, or with other dienes which form readily soluble complexes with rhodium. Preferred compounds which yield rhodium are e.g. di-µ-chloro-bis[η⁴-(Z,Z)-1,5-cyclooctadiene]dirhodium(I), di-µ-chloro-bis[η⁴-norbornadiene]-dirhodium(I), di-µ-trifluoroacetate-bis[η⁴-(Z,Z)- 1,5-cyclooctadiene]dirhodium(I), bis[η⁴-(Z,Z)-1,5-cyclooctadiene]rhodium(I) tetrafluoroborate or bis [η⁴-(Z,Z)-cyclooctadiene]rhodium(I) perchlorate, Di-µ-chloro-bis[η⁴-(Z,Z)-1,5-cyclooctadiene]diiridium(I) can be mentioned, for example, as a compound which yields iridium.

The novel transition metal tetrasulfonated diphosphine complexes of the present invention where the transition metal is rhuthenium, can be represented e.g. by the following formula Ru(Z)₂L            XIV wherein Z represents halogen or the group A—COO, wherein A represents lower alkyl, aryl, halogenated lower alkyl or halogenated aryl, wherein L represents a racemic or optically active diphosphine ligand of formulae I or II.

When A represents lower alkyl, A may be any lower alkyl as defined above. When A represents aryl, A may be any aryl including any substituted or unsubstituted aryl. When A is halogenated aryl, A may be any aryl substituted with any halogen, and A may include any arid substituted in more than one position with a halogen and/or any other substitution group. When Z is a halogen, any halogen may be used, such as bromine, iodine or chlorine. The aforemention ruthenium complexes can, in principle, be manufactured in a manner known per se. Conveniently and preferably, ruthenium-tetrasulfonated diphosphine complexes are manufactured, for example, by reacting a compound of the formula

[Ru(Z¹)₂L¹ᵣ]ₚ.(H₂O)_q        XV wherein Z¹ represents halogen or a group A¹—COO, A¹ represents lower alkyl or halogenated lower alkyl, L¹ represents a neutral ligand, r represents the number 1, 2 or 3, p represents the number 1 or 2 and q represents the number 0 or 1,
with a racemic or optically active diphosphine ligand of formulae I or II or by reacting a ruthenium complex of the formula Ru(CF₃COO)₂L         XVI wherein L represents a racemic or optically active diphosphine ligand of formulae I or II,
with a salt which yields the anion Z in which Z has the above significance.

When A¹ is lower alkyl, lower alkyl is as defined above. When Z¹ represents a halogen, any halogen may be used such as bromine, iodine or chlorine.

The term "neutral ligand" signifies, in the scope of the present invention, an exchangeable ligand. Any exchangeable ligand may be used. Preferred are for example, a diolefin, e.g. norbornadiene, (Z,Z)-1,5-cyclooctadiene etc., or also a nitrile such as acetonitrile, benzonitrile and the like. Where r represents the number 2 or 3, the ligands can be the same or different.

The ruthenium complexes of formula XV are known substances or analogues of known substances which can be obtained readily in a manner analogous to the preparation of the known substances, for example according to Albers, M. O. et al., J. Organomet. Chem. 272, C62-C66 (1984).

The reaction of a ruthenium complex of formula XV with a racemic or optically active diphosphine ligand of formulae I or II can be carried out in a manner known per se. The reaction can be conveniently carried out in an inert solvent. Any inert solvent may be used to catty out the reaction of a ruthenium complex of formulae XV with the ligand of formulae I or II. As examples of such inert solvents there can be mentioned e.g. water, lower alcohols such as, for example, methanol, ethanol etc., halogenated hydrocarbons such as methylene chloride, chloroform and the like, or also mixtures of such solvents. Moreover, the reaction can be carried out at a temperature between from about 0° C. to about 100° C., preferably between about 15° C. and about 60° C. When the reaction is carried out from about 15° C. to about 60° C. best results are obtained by strict exclusion of oxygen from the reaction.

The reaction of a ruthenium complex of formula XVI (obtainable from a complex of formula XV) with a salt which contains the anion Z can be carried out in a manner known per se. The term "a salt which yields the anion Z" signifies in the scope of the present invention, for example, ammonium salts, alkali metal salts or other suitable metal salts. In order to improve the solubility of such salts, crown ethers or the like can also be added in certain instances.

The transition metal tetrasulfonated diphosphine complexes of the present invention are useful as homogenous catalyst in asymmetric catalytic reactions, such as asymmetric hydrogenation, enantioselective isomerisation, and the like. Examples of asymmetric hydrogenations with the aforementioned complexes are the hydrogenation of substrates like allylic alcohols, for example geraniol (VIII), acylamidoacrylic acids or their salts, for example α-acetamido-cinnamic acid or its salts (IX), β-keto acids and their salts or esters, for example acetoacetic acid, methyl or lithium acetoacetate (X), α-keto acids and their salts, for example sodium pyruvate (XI) or α,β-unsaturated acids and their salts, for example compounds of formulae XII and XIII.

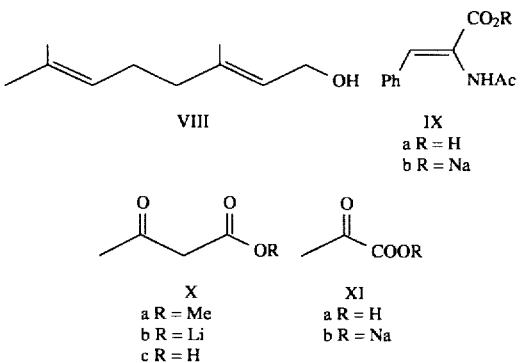

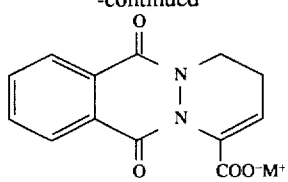

XII
a M⁻ = Et₃NH⁺
b M⁻ = Na⁺
c M⁻ = H⁺

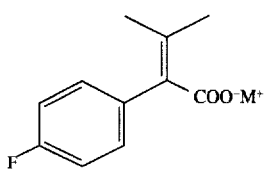

XIII
a M⁺ = Et₃NH⁺
b M⁺ = Na⁺
c M⁺ = H⁺

The hydrogenations may be performed in aqueous solvent systems, in biphasic systems consisting of water and a non-miscible organic phase or in organic systems alone with a subsequent removal of the catalyst by aqueous extraction all in manners known per se.

Complexes of compounds of formula I, wherein $R^1$ and $R^2$ are alike and signify methoxy and wherein m and n are 0, with ruthenium or rhodium are preferred for such hydrogenations. These complexes show particularly good catalytic properties in the asymmetric hydrogenation of the compounds listed above especially in the asymmetric hydrogenation of the salts of such compounds, that means in the asymmetric hydrogenation of the sodium salt of α-acetamino cinnamic acid (IXb), the lithium salt of β-keto acids, for example the lithium salt of acetoacetic acid (Xb), salts of α-keto acids, for example sodium pyruvate (XIb) or the sodium salts of α,β-unsaturated acids, for example compounds XIIb and XIIIb.

Furthermore, it has been demonstrated that the catalysts of the present invention can be efficiently separated from the product mixtures by methods known in the art. This is achieved by aqueous extraction of the catalyst from the product, from a solution of the product in an organic solvent or by adsorption of the catalyst onto ion exchange resins. The amount of metal removed by these operations is generally greater than 95% of the amount employed.

The ruthenium (Ru) catalyst and rhodium (Rh) catalyst derived from the ligand of formula I appears to be of equal enantioselectivity and of similar activity as the corresponding catalyst derived from the non-sulfonated ligand in these hydrogenations. In other words these are the first examples of highly efficient aqueous-phase asymmetric hydrogenations with Ru catalysts or Rh-catalysts derived from a sulfonated diphosphine ligand. This also proves the validity of the inventive concept of introducing the sulfonato group in the para position of the P-phenyl groups in order to exclude steric effects on the asymmetric induction in the catalytic step. In these reactions a quantitative conversion and a high chemical as well as optical yield can be achieved. The optical induction is usually very high and the enantiomeric excess (e.e.) is typically above 90%.

The following examples serve to illustrate the invention and do not in any manner represent a limitation.

In the examples the selected abbreviations have the follow meanings:

h hour
m.p. melting point
THF tetrahydrofuran
EtOAc ethyl acetate
c concentration
ee enantiomeric excess
GC Gaschromatography
cod 1,5-cyclooctadiene
nbd norbornadiene All experiments were carried out under an atmosphere of deoxygenated argon. Solvents were dried and distilled under argon before use. The metal diphosphine complexes were prepared using Schlenk techniques.

¹H-NMR spectra were recorded at 250 MHz (Bruker AC 250E) and 270 MHz (Bruker HX 270), chemical shifts in ppm (δ) with TMS as internal standard. The solvent used was CDCl₃ unless otherwise specified. The abbreviation have the following significances, m=multiplet, s=singulett, sbr.=singulett broad, mbr.=multiplet broad.

The starting material [Ru(OCOCF₃)₂(cod)]₂ was synthesized as described in Tetrahedron Asymmetry 1991, 2, 51. Indole was of technical purity, [Rh(nbd)Cl]₂ and other chemicals are commercially available and were used without further purification. [Rh(cod)₂]BF₄ and [Rh(nbd)₂]BF₄ were prepared according to standard procedures. [(R)- and (S)-6,6'-Dimethoxybiphenyl-2,2'-diyl]bis(phosphonic dichloride) was synthesized as reported in EP-A-530 335.

EXAMPLE 1

Synthesis of (S)-6,6'-Dimethoxy-biphenyl-2,2'-bis(4,4'-phosphinediyldibenzene-sulfonic acid) Na salt (1:4)(=(S)-MeOBIPHEP-TS-Na)

1. Synthesis of p-Bromophenyl indol-1-yl sulfone

To a solution of 80.0 g (683 mmol) of indole and 23 g (67.7 mmol) of tetrabutylammonium hydrogen sulfate in 1300 ml of toluene was added 640 ml of 50% NaOH. The two phases were vigorously stirred at room temperature for 5 min. A solution of 255.6 g (1 mol) of p-bromobenzenesulfonyl chloride was added dropwise and the reaction was stirred at room temperature for 1.5 h. After phase separation, the organic phase was washed with H₂O, dried, filtered, concentrated to about 500 ml and filtered (700 g silica gel, toluene) to afford about 300 g of crystals and oil. This material was dissolved in about 250 ml of CH₂Cl₂ and 1 l of hexane. The solution was partially evaporated, then the resulting crystals were collected by filtration and dried in vacuo to afford 171 g of p-bromophenyl indol-1-yl sulfone as white crystals, m.p.: 105.9°–106.3°. An additional 24.8 g of p-bromophenyl indol-1-yl sulfone was isolated from the mother liquor.

2. Synthesis of (S)-6,6'-Dimethoxy-P2,P2,P2', P2'-tetrakis-[4-(indol-1-ylsulfonyl)-phenyl]-biphenyl-2,2'-bis-phosphine-P2,P2'-oxide A solution of 84 g (250 mmol) of p-bromophenyl indol-1-yl sulfone in 1 l of THF (distilled from Na/benzophenone) was cooled to −78° whereby the sulfone partially crystallized. A solution of 200 ml of 1.42M butyllithium in hexane was added at such a rate to keep the temperature; below −68°. The reaction was further stirred for 20 min and 84 g (302 mmol) of freshly prepared MgBr₂.Et₂O was added at once as a solid. The reaction mixture was allowed to warm up to room temperature and was further stirred for 30 min. The violet solution was cooled to −78° and 13.5 g (30.1 mmol) of [(S)-6,6'-dimethoxybiphenyl-2,2'-diyl]bis(phosphonic dichloride) was added at once as a solid. The reaction was stirred for 10 rain at −78° and was allowed to warm up to room temperature, then further stirred for 2.5 h at room temperature. The reaction mixture was cooled to 0°, treated with a saturated NH$_4$Cl solution, washed with saturated NaCl solution, dried and evaporated to afford 66 g of a yellow solid. After chromatography (850 g silica gel, hexane/EtOAc 1:1 –>EtOAc) and evaporation, the residue was dried in vacuo to afford 28 g of (S)-6,6'-dimethoxy-P2, P2, P2', P2'-tetrakis-[4-(indol-1-ylsulfonyl)-phenyl]-biphenyl-2, 2'-bis-phosphine-P2,P2'-oxide as yellow powder, m.p.: 202.1°–202.8°, $[\alpha]_D^{20}$=−37.8 (c=1.0; CHCl$_3$).

3. Synthesis of (S)-6,6'-Dimethoxy-P2,P2,P2',P2'-tetrakis-[4(indol-1-ylsulfonyl -phenyl]-biphenyl-2,2'-bis-phosphine To a solution of 27.0 g (20.3 mmol) of (S)-6,6'-dimethoxy-P2,P2,P2',P2'-tetrakis-[4-(indol1-ylsulfonyl)-phenyl]-biphenyl-2,2'- bis-phosphine-P2,P2'-oxide in 550 ml of xylene were added 206 ml (865 mmol) of tributylamine and 82.6 ml (817 mmol) of trichlorosilane. The milky solution was refluxed for 7 h. After cooling the reaction to room temperature, a solution of 425 ml of 30% NaOH was added at such a rate as to keep the temperature below 22°. The reaction mixture was stirred at room temperature for 30 min. Then 200 ml of xylene was added and after phase separation the water phase was extracted with xylene. The combined organic phases were washed with saturated NaCl solution, dried, filtered and concentrated to about 500 ml. The excess of reagents was distilled in vacuo and the residue further dried under the previous conditions. The yellow residue (23 g) was dissolved in EtOH/CH$_2$Cl$_2$2:1 (900 ml), the solution was evaporated to about 400 ml and kept overnight at 4°. The resulting crystals were filtered, washed with cold EtOH and dried in vacuo for 3 h to afford 22.56 g of (S)-6,6'-dimethoxy-P2,P2,P2',P2'-tetrakis-[4-(indol-1-ylsulfonyl)-phenyl]-biphenyl-2,2'-bis-phosphine as white crystals, m.p. 178.0°–179.5°. $[\alpha]_D^{20}$=−28.0 (c =1.0, CHCl$_3$).

4. Synthesis of (S)-MeOBIPHEP-TS-Na

To a stirred suspension of 22.5 g (17.3 mmol) of (S)-6, 6'-dimethoxy-P2, P2,P2',P2'-tetrakis-[4-(indol-1-ylsulfonyl)-phenyl]-biphenyl-2,2'-bis-phosphine in 450 ml of THF/MeOH 1:1 was added 42.4 ml (212.5 mmol) of 5N NaOH. The reaction mixture was refluxed for 5 h. After cooling the reaction to room temperature, the pH was adjusted to pH 7.0 with 25% and 2N HCl. Then the solvent was evaporated and the residue was dried in vacuo for 1 h. After removal of the free indole by extraction with toluene, the residue was dried in vacuo for 2 h to afford 27.2 g of crude (S)-6,6'-dimethoxybiphenyl-2,2'-phosphinediyldibenzenesulfonic acid) Na salt (1:4) as white powder. This material was chromatographed on ca.1100 ml of Mitsubishi gel CHP20P (75–150 µ), and elution was performed with deoxygenated water. After evaporation of the NaCl free fractions, the residue was dried in vacuo for 2 h to afford 14.3 g of (S)-6,6'-dimethoxybiphenyl-2,2'-bis(4,4'-phosphinediyldibenzenesulfonic acid) Na salt as yellowish crystals. $[\alpha]_D^{20}$=+65.1 (c=1.0, MeOH).

EXAMPLE 2

Synthesis of (R)-6,6'-Dimethoxy-biphenyl-2,2'-bis(4,4'-phosphinediyldibenzene-sulfonic acid) Na salt (1:4)(=(R)-MeOBIPHEP-TS-Na)

1. Synthesis of (R)-6,6'-Dimethoxy-P2,P2,P2',P2'-tetrakis-[4-(indol-1-ylsulfonyl)-phenyl]-biphenyl-2,2'-bis-phosphine-P2,P2'-oxide An analogous experiment as described in Example 1, 2. with 5.9 g (13.1 mmol) of (R)-bis(phosphoric dichloride) afforded 12.3 g (71%) of (R)-6,6'-dimethoxy-P2, P2,P2',P2'- tetrakis-[4-(indol-1-ylsulfonyl)-phenyl]-biphenyl-2,2'-bisphosphine-P2, P2'-oxide as white crystals. M.p.: 202.0°–202.9°.

2. Synthesis of the diphosphine ((R)-6,6'-Dimethoxy-P2, P2, P2', P2'-tetrakis:[4-(indol-1-ylsulfonyl)-phenyl]-biphenyl-2, 2'-bis-phosphine In an analogous experiment as described in Example 1, 3., 0.82 g (0.62 mmol) of the bis(phosphine oxide) was reduced to afford 0.56 g (70%) of (R)-6,6'-dimethoxy-P2, P2,P2', P2'-tetrakis-[4-(indol-1-ylsulfonyl)-phenyl]-biphenyl-2,2'-bis-phosphine as white crystals. M.p.: 176.0°–176.8°. $[\alpha]_D^{20}$=+27.8 (c=1.0, CHCl$_3$).

3. Synthesis of (R)-MeOBIPHEP-TS-Na

An analogous experiment as described in Example 1, 4. with 3.38 g (2.6 mol) of (R)-6,6'-dimethoxy-P2,P2,P2',P2'-tetrakis-[4-(indol-1-ylsulfonyl)-phenyl]-biphenyl-2,2'-bis-phosphine afforded 2.39 g (65%) of ((R)-MeOBIPHEP-TS-Na) as yellowish crystals. $[\alpha]_D^{20}$=−64.0 (c=1.0, MeOH).

EXAMPLE 3

Synthesis of ((S)-MeOBIPHEP-TS-Na)Ru(OCOCF$_3$)$_2$

A solution of 1.783 g (1.80 mmol) of (S)-MeOBIPHEP-TS-Na (from Example 1, 4) in 20 ml of MeOH was added to a solution of 0.783 g (0.90 mmol) of [Ru(OCOCF$_3$)$_2$(cod)]$_2$ in 10 ml of MeOH and stirred at 70° for 20 h. The resulting red solution was evaporated to dryness and the residue was washed with CH$_2$Cl$_2$/MeOH (9:1), CH$_2$Cl$_2$, pentane and dried in vacuo to afford ((S)-MeOBIPHEP-TS-Na)Ru(OCOCF$_3$)$_2$ as an orange-yellow powder in nearly quantitative yield. $^1$H-NMR (CD$_3$OD): 7.87–7.8 (m, 4H); 7.68–7.58 (m, 4H); 7.52–7.47 (m, 4H); 7.3–7.22 (m, 4H); 7.05–6.98 (m, 4H); 6.61–6.55 (m, 2H), 3.44(s, 2OCH$_3$); 3.34 (s, ca.1.5 mol equiv. MeOH).

EXAMPLE 4

1. Synthesis of [((S)-MeOBIPHEP-TS-Na)Rh(cod)]BF$_4$

A solution of 495 mg (0.5 mmol) of (S)-MeOBIPHEP-TS-Na (from Example 1.4.) in 15 ml of MeOH was added to a red solution of 203 mg (0.5 mmol) of Rh(cod)$_2$BF$_4$ in 10 of MeOH and stirred at room temperature for 4 h. The resulting orange solution was evaporated to dryness and the residue was washed with THF, Et$_2$O, pentane and dried in vacuo at 50° to afford ((S)-MeOBIPHEP-TS-Na)Rh(cod)BF$_4$ as an orange powder in nearly quantitative yield. $[\alpha]_D^{20}$=−13.4 (c=1.0, MeOH). $^1$H-NMR (D$_2$O):7.95–7.6(m, 16H); 7.5–7.4 (m, 2H); 7.25 (t, J=8, 2H); 6.62 (d, J=8, 2H); 4.92 (mbr., 2 olefin. H); 4.55 (mbr.,2 olefin. H); 3.4 (s, 2OCH$_3$); 3.34 (s, ca. 1.3 mol equiv. MeOH); 2.69–2.48 (m, 2H); 2.48–2.3 (m, 2H); 2.25–2.1 (m, 4H).

2. Synthesis of [((S)-MeOBIPHEP-TS-Na)Rh(nbd)]BF$_4$

An analogous experiment with Rh(nbd)$_2$BF$_4$ afforded, after a reaction at room temperature for 22 h, ((S)-MeOBIPHEP-TS-Na)Rh(nbd)BF$_4$ as an orange powder in nearly quantitative yield. $[\alpha]_D^{20}$ =+34.2 (c 0.5, MeOH). $^1$H-NMR (D$_2$O): 8.0–7.63 (m, 16H); 7.4–7.2 (m, 4H); 6.62 (d, J=8, 2H); 5.1–4.95(m, 4 olefin H); 4.02 (sbr., 2 methine H); 3.39 (s, 2OCH$_3$); 3.34 (s, ca. 0.7 mol equiv. MeOH); 1.6 (sbr.,—CH$_2$—).

3. Synthesis of ((S)-MeOBIPHEP-TS-Na)Rh(nbd)Cl

An analogous experiment with [Rh(nbd)Cl]$_2$ afforded, after a reaction at room temperature for 18 h, ((S)-MeOBIPHEP-TS-Na)Rh(nbd)Cl as an orange powder in nearly quantitative yield. $[\alpha]_D^{20}$=+19.0 (c=0.6, MeOH). $^1$H-NMR (D$_2$O): 7.95–7.65 (m, ca. 16H); 7.35–7.15 (m, 4H); 6.62 (dbr., J=8, 2H); 5.1–4.95 (m, 4 olefin. H); 4.02 (sbr., 2 methine H); 3.39 (s, 20CH$_3$); 3.34 (s, ca. 1.2 mol equiv. MeOH); 1.58 (sbr.,—CH$_2$—).

EXAMPLE 5

Hydrogenations of substrates VIII, IX, X or XI (Tables 1 and 2)

All experiments were carried out at ca. 30° or 50° in septum stoppered 50 ml glass flasks in a shaking rack hydrogenator. To a solution of the catalyst (20–80mg) in MeOH or H$_2$O(20 ml) was added the substrate as a solid or as a solution. The sodium or ammonium salts of the carboxylic acids were formed by the reaction of an equimolar amount of the acid with the corresponding base. The initial pressure was set to 10 bar H$_2$ and the reaction flask was shaken and occasionally repressurized with H$_2$. Then, the reaction solution was evaporated. The optical purity and/or ee were measured on the residue or on the catalyst free reaction products (catalyst was removed by solvent/H$_2$O extraction, or chromatography, or distillation). The percentage of conversion was determined by $^1$H-NMR. (cf. Tables 1 and 2).

EXAMPLE 6

Catalyst extraction

A solution of 10.17 g (65.93 mmol) of geraniol (VIII) and 130 mg (0.099 mmol) of ((S)-MeOBIPHEP-TS-Na)Ru(O-COCF$_3$)$_2$ in 100 ml of MeOH was hydrogenated at about 30° for 18 h in 5 portions of 20 ml. The reaction solutions were combined and evaporated to dryness. To the residue (yellowish oil and solid) was added 100 ml of toluene and 100 ml of H$_2$O and the mixture was vigorously stirred at room temperature After phase separation, the aqueous phase was extracted with toluene, then the combined organic phases were extracted with H$_2$O, dried and evaporated to dryness to afford 10.32 g of a yellowish oil. This residue was found to contain 17 ppm Ru, that means 1.8% of the amount of ruthenium contained in the catalyst used (cf. Table 1, Entry 6).

In an analogous experiment, 4.0 g (25.9 mmol) of geraniol (VIII) was hydrogenated in the presence of 106 mg (0.081 mmol) of ((S)-MeOBIPHEP-TS-Na)Ru(OCOCF$_3$)$_2$ in MeOH at about 30° for 22 h. The resulting solution was chromatographed on 35 g of Amberlite™ A26 (-N(CH$_3$)$_3$$^+$ $^-$)(elution with MeOH) and evaporated to dryness to afford 4.2 g of a yellowish oil. This residue was found to contain 55 ppm of Ru, that means 2.8% of the amount of ruthenium in the catalyst used (cf. Table 1, Entry 5).

TABLE 1

Asymmetric Hydrogenation of Geraniol (VIIII) with ((S)-MeOBIPHEP-TS-Na)Ru(OCOCF$_3$)$_2$ as catalyst

| | Substrate VIII | | Cat. | | Yield | GC[a] | | ee of A[b] | Product/catalyst | Ruthenium in product | | Ruthenium in aqu. phase | |
|---|---|---|---|---|---|---|---|---|---|---|---|---|---|
| Entry | [g] | c [%] | [mmol] | S/C | [g] | A [%] | B [%] | [%] (R) | separation | [ppm][c] | [%][d] | [mg][e] | [%][d] |
| 1 | 1.2 | 6 | 0.078 | 100 | 1.27 | 92 | 6 | 71 | CH$_2$Cl$_2$/H$_2$O | 44 | 0.7 | | |
| 2 | 3.6 | 36 | 0.042 | 560 | 3.58 | 93 | 5 | 36 | CH$_2$Cl$_2$/H$_2$O | 36 | 3.1 | 3.4 | 81 |
| 3 | 4.0 | 13 | 0.082 | 304 | 4.18 | 97 | 1 | 55 | MeOH/resin[f] | 106 | 5.4 | | |
| 4 | 4.0 | 13 | 0.094 | 281 | 4.08 | 94 | 1 | 34 | MeOH/resin[g] | 110 | 4.7 | | |
| 5 | 4.0 | 13 | 0.081 | 320 | 4.20 | 91 | 8 | 65 | MeOH/Amberlite A26[g] | 55 | 2.8 | | |
| 6 | 10.2 | 10 | 0.099 | 660 | 10.32 | 94 | 0.5 | 89 | Toluene/H$_2$O | 17 | 1.8 | 7.2 8.2[c] | 72 82 |

[a]GC: Column CPMS/1701, ID = 0.32 mm, L = 25 m; Inj. = 220°, Det. = 250; Program: 100° for 3 min, 100–130° at 3°/min; Area %, total of all peaks = 100%.
[b]Determined by GC after derivatization with (S)-Troloxmethylether.
[c]Ru determination by X-ray fluorescence.
[d]% of Ru found based on used amount of Ru-catalyst = 100%.
[e]Ru determination by atom absorption.
[f]The MeOH solution was stirred in the presence of the ion exchange resin (polysiloxane with pendent tripropyl-methyl ammonium side chains).
[g]The MeOH solution was filtered through a column containing the ion exchange resin.

TABLE 2

Asymmetric Hydrogenation with Water-Soluble Catalysts [((S)-1) = ((S)-MeOBIPHEP-TS-Na)]

| Entry | Substrate | | | Catalyst | S/C | Solvent | c [%] | Temp. [°C.] | t [h] | Conv.[a] [%] | op[b] or ee[c] [%] |
|---|---|---|---|---|---|---|---|---|---|---|---|
| 1 | CO$_2$R | | R = H | ((S)-1)Ru(OCOCF$_3$)$_2$ | 148 | MeOH | 7 | 25 | 4 | 100 | 75 (S)[b,e] |
| 2 | | | R = H | ((S)-1)Ru(OCOCF$_3$)$_2$ | 75 | H$_2$O | 2 | 25 | 66 | 45 | 82 (S)[b] |
| 3 | | | R = H | ((S)-1)Rh(cod)BF$_4$ | 43 | H$_2$O | 2 | 25 | 6 | 71 | 38 (R)[b] |
| 5 | Ph | NHAc | R = Na | ((S)-1)Rh(cod)BF$_4$ | 93 | H$_2$O | 2 | 25 | 66 | 100 | 66 (R)[b] |
| 6 | IX | | R = Na | ((S)-1)Rh(nbd)BF$_4$ | 103 | H$_2$O | 9.8 | 25 | 66 | 100 | 53 (R)[b] |

TABLE 2-continued

Asymmetric Hydrogenation with Water-Soluble Catalysts [((S)-1) = ((S)-MeOBIPHEP-TS-Na)]

| Entry | Substrate | | Catalyst | S/C | Solvent | c [%] | Temp. [°C.] | t [h] | Conv.[a] [%] | op[b] or ee[c] [%] |
|---|---|---|---|---|---|---|---|---|---|---|
| 7 | 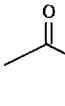 | R = Me | ((S)-1)Ru(OCOCF$_3$)$_2$ | 2575 | MeOH | 33 | 50 | 44 | 90 | 93 (S)[c] |
| 8 | | R = Me | ((S)-1)Ru(OCOCF$_3$)$_2$ + 2HCl | 2015 | MeOH | 33 | 50 | 44 | 100 | 89 (S)[c] |
| 9 | X | R = Me | ((S)-1)Rh(nbd)(Cl) + 2HCl | 2726 | H$_2$O | 33 | 50 | 44 | 64 | 53 (R)[d] |
| 15 | 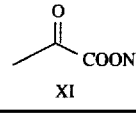 | | ((S)-1)Ru(OCOCF$_3$)$_2$ | 379 | MeOH | 5 | 50 | 16 | 6 | 69 (S)[d] |
| 16 | XI | | ((S)-1)Ru(OCOCF$_3$)$_2$ | 267 | H$_2$O | 5 | 50 | 16 | 18 | 35 (S)[d] |

[a]Conversions were determined by $^1$H-NMR.
[b]Optical purity calc. on the basis of $[\alpha]^{20}_D = 40.0$ (c = 1.0, CHCl$_3$) for (S)-(+)- or (R)-(−)-N-acetyl-phenylalanine.
[c]Detemined by GC after derivatization with (S)-Troloxmethylether.
[d]Optical purity calc. on the basis of $[\alpha]^{20}_D = 12.0$ (c = 1.0, H$_2$O) for (R)-(+)- or (S)-(−)-sodium lactate.
[e]Hydrogenation of 7.0 g of IX with 0.230 mmol of (S)-1, MeOH soln. stirred in the presence of the ion exchange resin (polysiloxane with pendent tripropyl-methylammonium side chains): ruthenium in the product = 150 ppm (4.5% of the used amount).

EXAMPLE 7

Hydrogenation of geraniol VIII

A 185 ml autoclave was charged in a glove box (O$_2$ content<1 ppm) with 8.8 g geraniol VIII [(E)-3,7-dimethyl-2,6-octadien-1-ol], 75.2 mg ((S)-MeO-BIPHEP-TS-Na)Ru(OCOCF$_3$)$_2$, 31 ml ethyl acetate and 8 ml water. The hydrogenation was effected under vigorous stirring at 20° C. and 60 bar. After 68 hours the conversion amounted to 96%. The organic phase was separated and evaporated at 45° C./17 mbar. The residue consisted 92% (R)-Citronellol (A) and 4% by-product B. For purification the clear residue was destilled at 60° C./0.2 mbar. There were obtained 7.7 g (R)-Citronellol (A) [(R)-3,7-dimethyl-6-octen-1-ol] as a colourless oil; e.e. 97%.

EXAMPLE 8

Hydrogenation of 3,4,6,11-tetrahydro6,11-dioxo-pyridazo [1,2-a]phthalazin- 1-carboxylic acid ("dehydrophthaloyl acid")(XII)

1. Hydrogenation of the triethylammonium salt XIIa

In a glove box (argon-atmosphere, O$_2$-content<1 ppm) a 5 ml measuring flask was charged with 5.2 mg (0.0039 mmol) of ((S)-MeOBIPHEP-TS-Na)Ru(OCOF$_3$)$_2$ and filled to the graduation mark with 5 ml of degassed water. The suspension was stirred with a magnetic stirring bar for 15 min at room temperature. A clear yellow solution formed. In the glove box a 500 ml stirred stainless steel autoclave was charged with 10.1 g (39.1 mmol) of dehydrophthaloyl acid, 145 ml of degassed water and 3.96 g (39.1 mmol) of degassed triethylamine. To this suspension 5 ml of the above catalyst solution was added and the autoclave was then sealed, pressurized with 6 bar of argon and removed from the glove box. The autoclave was connected to a hydrogenation line, which was thoroughly flushed with hydrogen. The argon in the autoclave was replaced by 40 bar of hydrogen, and the hydrogenation was carried out by stirring at 60° and 40 bar. After a reaction time of 21 h (conversion>99 GC-area %) the autoclave was vented and 126.6 g of the clear yellow reaction mixture (corresponding to 30.2 mmol of (-)-1,2,3,4,6,11-hexahydro-6,11-dioxopyridazo[1,2-b]phthalazine-1-carboxylic acid was transferred to a 500 ml four-necked, round-bottomed flask fitted with a thermometer, addition funnel and a motor-driven paddle stirrer. The stirred solution was acidified at 5° by dropwise addition of 35 ml of 1N aqueous hydrochloric acid. During the addition a precipitate formed. The suspension was stirred at 5°–7° for 2 h. The crystals were collected by filtration, washed with water (5×40 ml) and dried at 60°/20 mbar for 18 h and at 60°/0.05 mbar for 16 h. Yield 7.85 g of (-)-1,2,3,4,6,11-hexahydro-6,11-dioxopyridazo-[1,2-b]phthalazine-1-carboxylic acid as off-white crystals; ee≤99% (determined by HPLC on a chiral α-AGP-column, (α-acid glycoprotein)); purity 98.0 GC-area %.

2. Hydrogenation of the sodium salt XIIb

In a glove box (argon-atmosphere, O$_2$-content<1 ppm) a 5 ml measuring flask was charged with 25.8 mg (0.0196 mmol) of ((S)-MeOBIPHEP-TS-Na)-Ru(OCOF$_3$)$_2$ and filled to the graduation mark with 5 ml of degassed water. The suspension was stirred with a magnetic stirring bar for 15 min at room temperature. A clear yellow solution formed. In a 250 ml round-bottomed flask, 10.1 g (39.1 mmol) of dehydrophthaloyl acid were suspended in 60 ml of degassed water. To this suspension 37.2 ml of degassed 1N aqueous sodium hydroxide solution was added dropwise at 1°–3°. The evacuated flask was transferred into the glove box, where the suspension was degassed by evacuation and flushing with argon (eight cycles). The suspension was transferred in the glove box into a 500 ml stirred stainless steel autoclave, and the 5 ml of the above catalyst solution and 48 ml of degassed water were added. The autoclave was then sealed, pressurized with 6 bar of argon and removed from the glove box. The autoclave was connected to a hydrogenation line, which was thoroughly flushed with hydrogen. The argon in the autoclave was replaced by 40 bar of hydrogen and the hydrogenation was carried out by stirring at 60° and 40 bar. After a reaction time of 21 h (conversion>99 GC-area %) the autoclave was vented and 116.3 g of the yellow reaction mixture (corresponding to 28.1 mmol of (-)-1,2,3,4,6,11-hexahydro-6,11-dioxopyridazo[1,2-b]phthalazine-1-carboxylic acid was transferred to a 500 ml four-necked, round-bottomed flask fitted with a thermometer, addition funnel and a motor-driven paddle stirrer. The stirred solution was acidified at 2° by dropwise addition of 5 ml of 25% aqueous hydrochloric acid. During the addition a precipitate formed. The suspension was stirred at 3°–5° for 2 h. The crystals were collected by filtration, washed with water and dried at 60°/20 mbar for 4 h and at 60°/0.05 mbar for 18 h. Yield 7.3 g of (-)-1,2,3,4,6,11-hexahydro-6,11-dioxopyridazo[1,2-b]phthalazine-1-carboxylic acid as off-white crystals; ee>99%; purity 98.7 GC-area %.

EXAMPLE 9

Hydrogenation of 3-methyl-2-(p-fluorophenyl)crotonic acid (XIII)

1. Hydrogenation of the triethylammonium salt XIIIa

In a glove box (argon-atmosphere, $O_2$-content<1 ppm) a 10 ml measuring flask was charged with 16.9 mg (0.013 mmol) of ((S)-MeOBIPHEP-TS-Na)Ru(OCOF$_3$)$_2$ and filled to the graduation mark with 10 ml of degassed water. The suspension was stirred with a magnetic stirring bar for 15 min at room temperature A clear yellow solution formed. In the glove box a 30 ml stainless steel autoclave fitted with a magnetic stirring bar was charged with 0.5 g (2.57 mmol) of 3-methyl-2-(p-fluorophenyl)crotonic acid, 7.5 ml of degassed water and 0.26 g (2.57 mmol) of degassed triethylamine. To this suspension 2.0 ml of the above catalyst solution was added and the autoclave was then sealed, pressurized with 6 bar of argon and removed from the glove box. The autoclave was connected to a hydrogenation line, which was thoroughly flushed with hydrogen. The argon in the autoclave was replaced by 60 bar of hydrogen and the hydrogenation was carried out by stirring at 20° and 60 bar. After a reaction time of 21 h the autoclave was vented. The light yellow reaction mixture was transferred to a 50 ml separatory funnel, acidified at 20–25° by adding 2.7 ml of 1N aqueous hydrochloric acid and extracted with ether. The combined ether extracts were washed with saturated aqueous sodium chloride solution, dried over sodium sulfate and concentrated to dryness by rotary evaporation. Distillation of the reddish residue at 160° and 0.1 mbar afforded 0.48 g of (R)-2-(4-fluorophenyl)-3-methylbutyric acid as a colorless oil, which solidified on standing at room temperature; ee 84% (determined by GC on a chiral permethylated β-cyclodextrin column); purity>99 GC-area %.

2. Hydrogenation of the sodium salt

In a glove box (argon-atmosphere, $O_2$-content<1 ppm) a 10 ml measuring flask was charged with 16.9 mg (0.013 mmol) of ((S)-MeOBIPHEP-TS-Na)Ru(OCOF$_3$)$_2$ and filled to the graduation mark with 10 ml of degassed water. The suspension was stirred with a magnetic stirring bar for 15 min at room temperature. A clear yellow solution formed. In the glove box a 30 ml stainless steel autoclave fitted with a magnetic stirring bar was charged with 0.5 g (2.57 mmol) of 3-methyl-2-(p-fluorophenyl)crotonic acid, 4.93 ml of degassed water and 2.57 mmol (2.57 mmol) of a degassed aqueous 1N sodium hydroxide solution. To this suspension 2.0 ml of the above catalyst solution was added and the autoclave was then sealed, pressurized with 16 bar of argon and removed from the glove box. The autoclave was connected to a hydrogenation line, which was thoroughly flushed with hydrogen. The argon in the autoclave was replaced by 60 bar of hydrogen and the hydrogenation was carried out by stirring at 20° and 60 bar. After a reaction time of 21 h the autoclave was vented. The light yellow reaction mixture was transferred to a 50 ml separatory funnel, acidified at 20–25° by adding 2.7 ml of 1N aqueous hydrochloric acid and extracted with ether. The combined ether extracts were washed with saturated aqueous sodium chloride solution, dried over sodium sulfate and concentrated to dryness by rotary evaporation. Distillation of the reddish residue at 160° and 0.1 mbar afforded 0.47 g of (R)-2-(4-fluorophenyl)-3-methylbutyric acid as a colorless oil, which solidified on standing at room temperature; ee 80%; purity>99 GC-area %.

We claim:

1. Water-soluble racemic or optically active compound of the formulae

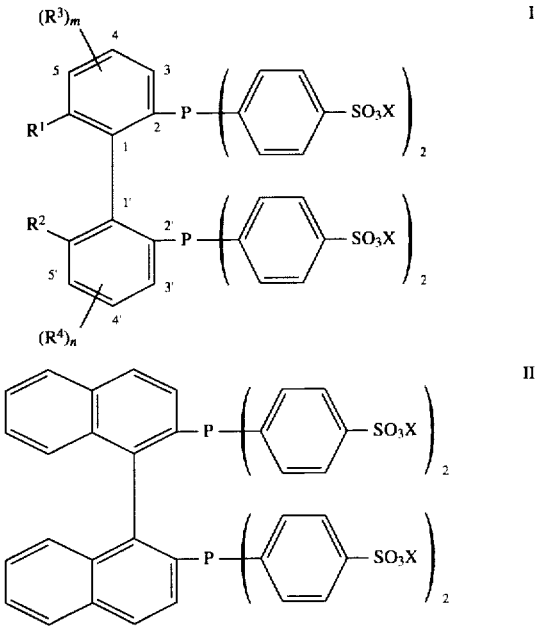

wherein $R^1$, $R^2$, $R^3$ and $R^4$ independently are lower alkyl or lower alkoxy;

m and n are 0, 1 or 2;

X is hydrogen, an alkali metal, earth alkali metal or an ammonium ion;

$R^3$ is in position 4 or 5; and $R^4$ is in position 4' or 5'.

2. A compound of formula I of claim 1, wherein m and n is 0.

3. A compound of formula I of claim 1, wherein $R^1$ and $R^2$ are the same and signify methyl or methoxy.

4. A compound of formula I of claim 1, wherein m and n are 0, and $R^1$ and $R^2$ are the same and signify methyl or methoxy.

5. A compound of formula I of claim 1, wherein $R^1$ and $R^2$ are independently methoxy.

6. A compound of formula I of claim 1, wherein m, and n are 0, and $R^1$ and $R^2$ are independently methoxy.

7. The compound (R,S)-, (R)- or (S)-6,6'-dimethoxy-biphenyl-2,2'-bis(4,4'phosphinediyldibenzenesulfonic acid) Na salt (1:4).

8. A metal complex containing a compound of formula I of claim 1, complexed with a Group VIII metal.

9. A metal complex containing a compound of formula II of claim 1, complexed with a Group VIII metal.

10. A metal complex of claim 8, wherein the Group VIII metal is ruthenium, rhodium, palladium or iridium.

11. A metal complex of claim 9, wherein the Group VIII metal is ruthenium, rhodium, palladium or iridium.

12. A metal complex of claim 8 wherein the Group VIII metal is ruthenium.

13. A metal complex of claim 9, wherein the Group VIII metal is ruthenium.

14. A metal complex of claim 8, wherein the Group VIII metal is rhodium.

15. A metal complex of claim 9, wherein the Group VIII metal is rhodium.

16. The compound ((S)-6,6'-Dimethoxy-biphenyl-2,2'-bis(4,4'-phosphinediyl-dibenzenesulfonic acid)Na salt) ruthenium $(OCOF_3)_2$.

17. The compound [((S)-6,6'-Dimethoxy-biphenyl-2,2'-bis(4,4'-phosphine-diyl-dibenzenesulfonic acid)Na salt) rhodium (1.5-cyclooctadiene)]$BF_4$.

18. The compound [((S)-6,6'-Dimethoxy-biphenyl-2,2'-bis (4,4'-phosphinediyl-dibenzene sulfonic acid)Na salt) rhodium (norbornadiene)]$BF_4$.

19. The compound [((S)-6,6'-Dimethoxy-biphenyl-2,2'bis(4,4'-phosphinediyl-dibenzenesulfonic acid)Na salt) rhodium (norbornadiene)]Cl.

* * * * *